United States Patent [19]

LaPointe

[11] Patent Number: 5,321,106
[45] Date of Patent: Jun. 14, 1994

[54] ADDITION POLYMERIZATION CATALYST WITH OXIDATIVE ACTIVATION

[75] Inventor: Robert E. LaPointe, Midland, Mich.

[73] Assignee: The Dow Chemical Company, Midland, Mich.

[21] Appl. No.: 896,732

[22] Filed: Jun. 9, 1992

Related U.S. Application Data

[63] Continuation of Ser. No. 547,718, Jul. 3, 1990, abandoned.

[51] Int. Cl.$^5$ .............................. C08F 4/00; C08F 4/12
[52] U.S. Cl. ..................................... 526/126; 526/134; 526/170; 502/103; 502/117; 502/152; 502/155
[58] Field of Search ................. 526/90, 150, 170, 126, 526/134; 502/103, 117, 152, 155

[56] References Cited

U.S. PATENT DOCUMENTS

| | | | |
|---|---|---|---|
| 4,931,417 | 6/1990 | Miya et al. | 526/150 |
| 5,026,798 | 6/1991 | Canich | 502/103 X |
| 5,034,034 | 7/1991 | Ewen | 502/117 |
| 5,055,438 | 10/1991 | Canich | 502/117 |
| 5,064,802 | 11/1991 | Stevens et al. | 502/155 |
| 5,066,741 | 11/1991 | Campbell | 502/117 X |
| 5,096,867 | 3/1992 | Canich | 502/103 |
| 5,132,380 | 7/1992 | Stevens et al. | 502/117 X |
| 5,153,157 | 10/1992 | Hlatky et al. | 502/117 |

FOREIGN PATENT DOCUMENTS

| | | | |
|---|---|---|---|
| 0277004 | 8/1988 | European Pat. Off. | |
| WO87/03887 | 7/1987 | PCT Int'l Appl. | 502/103 |

OTHER PUBLICATIONS

Zambelli et al., Macromolecules, 1989, (22), pp. 2186-2189.
J.A.C.S., 109, 4111-4113 (1987) (no month available).
J.A.C.S., 110, 6255-6256 (1988) (no month available).
J.A.C.S., 108, 7410-7411 (1986) (no month available).
J.A.C.S., 107, 7219-7221 (1985) (no month avaiable).

*Primary Examiner*—Patrick P. Garvin

[57] ABSTRACT

Addition polymerization catalysts comprising a derivative of a Group 4 or Lanthanide metal compound prepared by oxidative activation, a process for preparation and an addition polymerization method utilizing such catalysts.

23 Claims, No Drawings

ADDITION POLYMERIZATION CATALYST WITH OXIDATIVE ACTIVATION

CROSS-REFERENCE TO RELATED APPLICATION

This is a continuation of application Ser. No. 07/547,718, filed Jul. 3, 1990 and now abandoned.

BACKGROUND OF THE INVENTION

This invention relates to compositions of matter that are useful as catalysts, to a method for preparing the compositions of these catalysts, and to a method of using the compositions as addition polymerization catalysts. More particularly, this invention relates to catalyst compositions, to a method of preparing these catalyst compositions and to a method for polymerizing olefins, diolefins and/or acetylenically unsaturated monomers wherein these catalysts are used.

The use of Ziegler-Natta type catalysts in the polymerization of addition polymerizable monomers is, of course, well known in the prior art. In general, these soluble systems comprise a Group 4 or Lanthanide metal compound and a metal alkyl cocatalyst, particularly an aluminum alkyl cocatalyst.

In U.S. Ser. No. 8,800, filed Jan. 30, 1987, and now abandoned (published in equivalent form as EP 277,004) there are disclosed certain bis(cyclopentadienyl) metal compounds formed by reacting a bis(cyclopentadienyl) metal complex with salts of Bronsted acids containing a non-coordinating compatible anion. The reference discloses the fact that such complexes are usefully employed as catalysts in the polymerization of olefins. For the teachings contained therein the aforementioned U.S. Ser. No. 8,800 (now abandoned) and EP 277,004 are herein incorporated in their entirety by reference thereto.

Disadvantageously it has now been found that catalysts prepared according to the foregoing technique are detrimentally affected by the presence of by-product amine compounds resulting from the catalyst formation. That is, the procedure of EP 277,004 involves an irreversible reaction between a ligand of the metal compound and a cation of the Bronsted acid salt. In practice such cations are generally trialkyl ammonium ions that result in the formation of a tertiary amine by proton transfer to the ligand during catalyst formation. Such amine compounds are undesirable components of the resulting catalyst due to their inhibiting effect on addition polymerizations.

It would be desirable if there were provided a addition polymerization catalyst that is activated in a manner that forms only noninterfering and inert byproducts.

In *J. Am. Ch. Soc.* 109, 4111–4113 (1987) there is disclosed a process for preparation of cationic zirconium (IV) benzyl complexes by one electron oxidation of d° organometallic compounds. The solvents employed in the preparation of the zirconium metallocenes were tetrahydrofuran or methylene chloride both of which interfere with the desired catalyst formation and or detrimentally affect subsequent olefin polymerizations. In addition the reference employed an oxidizing agent containing tetraphenylborate. Such anions, it has now been discovered, are unacceptable for use in an oxidation activation process for preparing addition polymerization catalysts.

It has now been discovered that the foregoing and other disadvantages of the prior art ionic olefin polymerization catalysts can be avoided or at least reduced with the catalysts of the present invention. In addition an improved catalyst activation procedure and improved addition polymerization processes are provided according to the present invention. It is, therefore, an object of this invention to provide improved ionic catalyst systems which are useful in the polymerization of addition polymerizable monomers including olefins, diolefins and/or acetylenically unsaturated monomers. It is another object of this invention to provide a method for preparing such improved catalysts. It is a further object of this invention to provide an improved polymerization process using such improved catalysts. It is still another object of this invention to provide such an improved catalyst which is not subject to formation of interfering compounds. Finally it is an object of this invention to provide such an improved catalyst which may permit better control of the product polymer molecular weight and molecular weight distribution.

SUMMARY OF THE INVENTION

In accordance with the present invention there is provided a catalyst useful for addition polymerizations, which catalyst is substantially lacking in amine byproducts, said catalyst corresponding to the formula:

$L_l MX^+ A^-$, wherein:

L independently each occurrence is an anionic or nonanionic ligand or ligand system;

M is a metal of group 4 or Lanthanide series of the periodic table;

X is a hydride or $C_{1-10}$ hydrocarbyl group;

l is an integer greater than or equal to 1; and $A^-$ is a monovalent compatible noncoordinating anion.

Further in accordance with the present invention there is provided a process for preparing the above addition polymerization catalyst comprising contacting a derivative of a group 4 or Lanthanide metal corresponding to the formula:

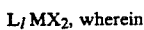
$L_l MX_2$, wherein

L, l, M, and X are as previously defined,
with an oxidizing agent which in reduced form is noninterfering with the resulting catalyst, said oxidizing agent comprising a cationic oxidizer and a compatible noncoordinating anion.

Preferably the oxidizing agent corresponds to the formula:

$$(Ox^{+a})_b(A^{-c})_d \qquad (I)$$

wherein:

$Ox^{+a}$ is a cationic oxidizer having a charge of (+a) capable of oxidizing the derivative of a Group 4 or Lanthanide metal;

$A^{-c}$ is a compatible noncoordinating anion having a charge of (−c); and b and d are integers selected to provide charge balance.

The catalysts may be prepared by contacting the derivative of a Group 4 or Lanthanide metal with the oxidizing agent optionally in an inert diluent such as an organic liquid.

DETAILED DESCRIPTION OF THE INVENTION

All reference to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering groups.

The term "anionic or nonanionic ligand or ligand system" refers to any ancillary, electron donating or electron sharing moiety. Such ligands include anionic ligands and neutral donor ligands.

Illustrative but nonlimiting examples of suitable anionic ligands include: R, $-R'(OR')_m OR$, $(OR')_m OR$, $-PR_2$, $-SR$, $-OR$, $-NR_2$, hydride, and organometalloid radicals comprising a Group 14 element wherein each of the hydrocarbyl substituents contained in the organic portion of said organometalloid, independently, contains from 1 to 20 carbon atoms. In these ligands:

R is a hydrocarbyl, silyl, germyl or a substituted hydrocarbyl, silyl, or germyl group of from 1 to 24 carbon, silicon, or germanium atoms;

R' is $C_{2-10}$ alkylene, and m is an integer from zero to ten.

Illustrative but non-limiting examples of suitable neutral donor ligands (L') include: ROR, $NR_3$, $PR_3$, and $SR_2$ wherein R is as above defined.

The term "cationic oxidizer" as used herein refers to an organic or inorganic ion having an oxidation potential sufficient to cause a molecular oxidation of the derivative of a Group 4 or Lanthanide metal so as to form a catalytic species. Generally and preferably the Group 4 or Lanthanide metal of the derivative compound is already in the highest atomic oxidation state. The process of the invention involves a molecular oxidation. Most preferred cationic oxidizers have an oxidation potential of at least +0.20 volt and preferably at least +0.25 volt.

As used herein, the recitation "compatible noncoordinating anion" means an anion which when functioning as a charge balancing anion in the catalyst system of this invention does not transfer an anionic substituent or fragment thereof to any cationic species thereby forming a neutral Group 4 or Lanthanide metal product. "Compatible anions" are anions which are not degraded to neutrality during catalyst preparation or use.

The recitation "metalloid", as used herein, includes nonmetals such as boron, phosphorus and the like which exhibit semi-metallic characteristics.

Preferred derivatives of Group 4 or Lanthanide compounds are those containing a metal of Group 4, especially, titanium and zirconium.

Further preferred derivatives correspond to the formula: L"MX$_2$, wherein:

L" is a divalent derivative of a substituted cyclopentadienyl group imparting a constrained geometry to the metal active site and containing up to 20 nonhydrogen atoms;

M is a metal of group 4 or the lanthanide series of the periodic table of the elements; and X independently each occurrence is hydride or alkyl, silyl, germyl, aryl, or a combination thereof having up to 20 carbon, silicon or germanium atoms.

By use of the term "constrained geometry" herein is meant that the metal atom is forced to greater exposure of the active metal site because of one or more substituents on the cyclopentadienyl or substituted cyclopentadienyl group forming a portion of a ring structure wherein the metal is both bonded to an adjacent covalent moiety and is held in association with the cyclopentadienyl or substituted cyclopentadienyl group through an $\eta^5$ bonding interaction. It is understood that each respective bond between the metal atom and the constituent atoms of the cyclopentadienyl or substituted cyclopentadienyl group need not be equivalent. That is the metal may be symetrically or unsymetrically π-bound to the cyclopentadienyl or substituted cyclopentadienyl group.

The geometry of the active metal site is further defined as follows. The centroid of the cyclopentadienyl or substituted cyclopentadienyl group may be defined as the average of the respective X, Y, and Z coordinates of the atomic centers forming the cyclopentadienyl or substituted cyclopentadienyl group. The angle, Θ, formed at the metal center between the centroid of the cyclopentadienyl or substituted cyclopentadienyl group and each other ligand of the metal complex may be easily calculated by standard techniques of single crystal X-ray diffraction. Each of these angles may increase or decrease depending on the molecular structure of the constrained geometry metal complex. Those complexes wherein one or more of the angles, Θ, is less than in a similar, comparative complex differing only in the fact that the constrain-inducing substituent is replaced by hydrogen have constrained geometry for purposes of the present invention. Preferably one or more of the above angles, Θ, decrease by at least 5% more preferably 7.5% compared to the comparative complex. Highly preferably, the average value of all bond angles, Θ, is also less than in the comparative complex.

Preferably, monocyclopentadienyl metal coordination complexes of group 4 or lanthanide metals according to the present invention have constrained geometry such that the smallest angle, Θ, is less than 115°, more preferably less than 110°, most preferably less than 105°.

Highly preferred derivative compounds are monocyclopentadienyl compounds corresponding to the formula:

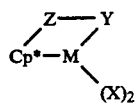

wherein:

M is a metal of group 4 or the lanthanide series of the periodic table of the elements;

Cp* is a cyclopentadienyl or substituted cyclopentadienyl group bound in an $\eta^5$ bonding mode to M;

Z is a divalent moiety comprising oxygen, boron, or a member of group 14 of the periodic table of the elements;

Y is a linking group comprising nitrogen, phosphorus, oxygen or sulfur or optionally Z and Y together form a fused ring system; and X is as previously defined.

After molecular oxidation the catalysts of the invention correspond to the formula:

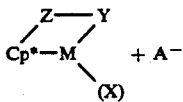

$$\text{II}$$

wherein Cp*, Z, M, X and A⁻ are as previously defined.

Each carbon atom in the cyclopentadienyl radical may be substituted or unsubstituted with the same or a different radical selected from the group consisting of hydrocarbyl radicals, substituted-hydrocarbyl radicals wherein one or more hydrogen atoms is replaced by a halogen atom, hydrocarbyl-substituted metalloid radicals wherein the metalloid is selected from Group 14 of the Periodic Table of the Elements, and halogen radicals. In addition two or more such substituents may together form a fused ring system. Suitable hydrocarbyl and substituted-hydrocarbyl radicals, which may be substituted for at least one hydrogen atom in the cyclopentadienyl radical, will contain from 1 to about 20 carbon atoms and include straight and branched alkyl radicals, cyclic hydrocarbon radicals, alkyl-substituted cyclic hydrocarbon radicals, aromatic radicals and alkyl-substituted aromatic radicals. Suitable organometalloid radicals include mono-, di- and trisubstituted organometalloid radicals of Group 14 elements wherein each of the hydrocarbyl groups contain from 1 to about 20 carbon atoms. More particularly, suitable organometalloid radicals include trimethylsilyl, triethylsilyl, ethyldimethylsilyl, methyldiethylsilyl, triphenylgermyl, trimethylgermyl and the like.

Most highly preferred complex compounds are amidosilane- or amidoalkanediyl- compounds corresponding to the formula:

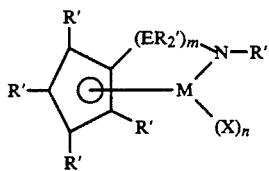

wherein:

M is a metal as previously defined, bound to an $\eta^5$-cyclopentadienyl group;

R' each occurrence is independently selected from the group consisting of hydrogen, silyl, alkyl, aryl and combinations thereof having up to 10 carbon or silicon atoms;

E is silicon or carbon;

X independently each occurrence is hydride, alkyl, or aryl of up to 10 carbons;

m is 1 or 2; and n is 1 or 2 depending on the valence of M.

Examples of the above most highly preferred metal coordination compounds include compounds wherein the R' on the amido group is methyl, ethyl, propyl, butyl, pentyl, hexyl, (including isomers), norbornyl, benzyl, phenyl, etc.; the cyclopentadienyl group is cyclopentadienyl, indenyl, tetrahydroindenyl, fluorenyl, octahydrofluorenyl, etc.; R' on the foregoing cyclopentadienyl groups each occurrence is hydrogen, methyl, ethyl, propyl, butyl, pentyl, hexyl, (including isomers), norbornyl, benzyl, phenyl, etc.; and X is methyl, neopentyl, trimethylsilyl, norbornyl, benzyl, methylbenzyl, phenyl, etc. Specific compounds include: (tert-butylamido)(tetramethyl-$\eta^5$-cyclopentadienyl)-1,2-ethanediylzirconium dimethyl, (tert-butylamido) (tetramethyl-$\eta^5$-cyclopentadienyl)-1,2-ethanediyltitanium dimethylbenzyl, (methylamido) (tetramethyl-$\eta^5$-cyclopentadienyl)-1,2-ethanediylzirconium dibenzhydryl, (methylamido) (tetramethyl-$\eta^5$-cyclopentadienyl)-1,2-ethanediyltitanium dineopentyl, (ethylamido)( tetramethyl-$\eta^5$-cyclopentadienyl)-methylenetitanium diphenyl, (tert-butylamido)dibenzyl(tetramethyl-$\eta^5$-cyclopentadienyl)silanezirconium dibenzyl, (benzylamido)dimethyl(tetramethyl-$\eta^5$-cyclopentadienyl)-silanetitanium di(trimethylsilyl), (phenylphosphido)-dimethyl (tetramethyl-$\eta^5$-cyclopentadienyl)silanezirconium dibenzyl, and the like.

In the most preferred embodiment -Z-Y- is an amidosilane or amidoalkane group of up to 10 nonhydrogen atoms, i.e. (tert-butylamido)(dimethylsilyl), (tert-butylamido)-1-ethane-2-yl, etc.

Derivative compounds which may be used in the preparation of the improved catalyst of this invention are covalently bonded metal compounds that are either devoid of reactive hydrogens or wherein potentially reactive hydrogens are protected by bulky protecting groups. Examples of suitable organyl substituents on such metal derivative compounds include norbornyl, neopentyl, trimethylsilyl, diphenylmethyl and the like. Illustrative, but not limiting examples of suitable derivative compounds include: tetranorbornyltitanium, tetrabenzylzirconium, tetraneopentyltitanium, diphenoxybis(trimethylsilyl)zirconium, bis(2,6-diisopropyl-4-methyl)phenoxy)dibenzyltitanium, tritertbutylsiloxy)-trimethylzirconium, dimethoxydibenzhydryltitanium, bis(2,4,6-trimethylphenoxy)dibenzyltitanium, butoxytris((trimethylsilyl)methyl)zirconium, dinorbornyldichlorotitanium, tribenzyltitanium hydride, etc.; cyclopentadienyl and bis(cyclopentadienyl) metal compounds such as bis(cyclopentadienyl)dimethylzirconium, cyclopentadienyltribenzylzirconium, cyclopentadienyltrimethyltitanium, cyclopentadienyltrimethylzirconium, bis(cyclopentadienyl) dineopentyltitanium, cyclopentadienyltri(diphenylmethyl)zirconium, bis(cyclopentadienyl)diphenylzirconium, cyclopentadienyltrineopentyltitanium, bis(cyclopentadienyl)di(m-tolyl)zirconium, biscyclopentadienyldi(p-tolyl)zirconium, and the like; hydrocarbylsubstituted cyclopentadienyl or bis(cyclopentadienyl) compounds such as (pentamethylcyclopentadienyl)(cyclopentadienyl)dimethylzirconium, bis(ethylcyclopentadienyl)dimethylzirconium, (pentamethylcyclopentadienyl)tribenzylzirconium, (n-butylcyclopentadienyl)trineopentyltitanium, cyclopentadienyldimethyltitanium hydride, bis(cyclopentadienyl)bis(diphenylmethyl)zirconium, bis(tert-butylcyclopentadienyl)bis(trimethylsilylmethyl)zirconium, bis(cyclohexylcyclopentadienyl)dimethylzirconium, (benzylcyclopentadienyl)di(m-tolyl)titanium chloride, (diphenylcyclopentadienyl)dinorbornylzirconium chloride, bis(methylcyclopentadienyl)diphenylzirconium, (tetraethylcyclopentadienyl)tribenzylzirconium, (propylcyclopentadienyl)(cyclopentadienyl)dimethylzirconium, bis(propylcyclopentadienyl)dimethylzirconium, (n-butyl cyclopentadienyl)dimethyl(n-butoxy)-titanium, cyclopentadienyldiphenylisopropoxyzirconium, cyclohexylmethylcyclopentadienyl)cyclopentadienyldibenzylzirconium, bis((cyclohexyl)methylcyclopentadienyl)dibenzylzirconium, bis(cyclopentadienyl) zirconium dihydride, benzylcyclopentadienyldimethylhafnium, bis(indenyl)dibenzylzirconium, (tert-butylamido)dimethyl(tetramethyl-$\eta^5$-cyclopentadienyl)silane dibenzylzirconium, (benzylamido)dimethyl(tetraethyl-$r\eta^5$-cyclopentadienyl)silane dibutyltitanium, and the like; metal hydrocarbyl-substituted cyclopentadienyl metal compounds such as ((trimethylsilyl)-cyclopentadienyl)trimethylzirconium, bis((trimethylgermyl)cyclopentadienyl)dimethyltitanium, ((trimethylstannyl)cyclopentadienyl)tribenzylzirconium, ((pentatrimethylsilyl)cyclopentadienyl)(cyclopentadienyl)dimethylzirconium, bis((trimethylsilyl)cyclopentadienyl)dimethylzirconium, penta((trimethylsilyl)cyclopentadienyl)tribenzyltitanium, bis((trimethylgermyl)cyclopentadienyl)diphenylhafnium, and the like; halogen-substituted cyclopentadienyl compounds such as ((trifluoromethyl)cyclopentadienyl)(cyclopentadienyl)dimethylzirconium, bis((trifluoromethyl)cyclopentadienyl)dinorbornylzirconium, ((trifluoromethyl)cyclopentadienyl)tribenzylzirconium, and the like; silyl-substituted (cyclopentadienyl)metal compounds such as bis(cyclopentadienyl )di(trimethylsilyl)zirconium, cyclopentadienyltri(phenyldimethylsilyl)zirconium, and the like; bridged cyclopentadienylmetal compounds such as methylenebis ((cyclopentadienyl)-dimethylzirconium), ethylene-bis-((cyclopentadienyl)-dibenzylzirconium), (dimethylsilylene)-bis-((cyclopentadienyl)dimethyltitanium), methylene-bis-(cyclopentadienyl)di(trimethylsilyl)zirconium, (dimethylsilylene) bis(cyclopentadienyldineopentylhafnium), ethylene-bis-(tetrahydroindenyl)-zirconium dibenzyl, dimethylsilylene(fluorenyl)(cyclopentadienyl)-titanium dimethyl, and the like.

Other compounds which are useful in the catalyst compositions of this invention, especially compounds containing other Group 4 or Lanthanide metals, will, of course, be apparent to those skilled in the art.

Compounds useful as oxidizing agents in the preparation of the compounds of this invention will comprise a cationic oxidizer, and one or more compatible noncoordinating anions, as previously explained.

In a preferred embodiment $A^{-c}$ of previous formula (I) comprises an anion which is a single coordination complex comprising a plurality of lipophilic radicals covalently coordinated to and shielding a central formally charge-bearing metal or metalloid atom, which anion is bulky and stable under the oxidation and subsequent polymerization conditions, and which anion is compatible with and noncoordinating towards the resulting Group 4 or Lanthanide metal containing catalyst. The anion is employed only to provide charge balance without interfering with the oxidizing ability of $Ox^{+a}$ or the catalytic properties of the resulting catalyst. Any metal or metalloid capable of forming a coordination complex which is stable under the reaction conditions of the present invention may be contained in the anion. Suitable metals include, but are not limited to, aluminum, gold, platinum and the like. Suitable metalloids include, but are not limited to, boron, phosphorus, silicon and the like. Oxidizing agents containing anions comprising a coordination complex containing a single boron atom are most preferred.

Anions comprising boron which are particularly useful in the preparation of catalysts of this invention may be represented by the following general formula:

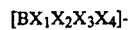

[$BX_1X_2X_3X_4$]- wherein:
B is boron in a valence state of 3;

$X_1$ to $X_4$ are the same or different nonreactive, organyl or silyl radicals containing from 6 to 20 carbon or silicon atoms. In addition two or more of $X_1$ to $X_4$ may be linked to each other through a stable bridging group. Preferably $X_1$ to $X_4$ lack reactive hydrogen moieties. That is, the radicals are either devoid of hydrogen, contain only hydrogen in nonactivated positions or contain sufficient steric hinderence to protect potentially active hydrogen sites. Examples of suitable radicals for $X_1$ to $X_4$ are perfluorinated hydrocarbyl radicals containing from 1 to 20 carbon atoms, 3,4,5-trifluorophenyl, 3,5-di(trifluoromethyl)phenyl, etc.

A most highly preferred compatible, non-coordinating, anion is tetra(pentafluorophenyl)borate.

Suitable organic cationic oxidizers for use according to the present invention include ferrocenium ions, bisindenyl Fe(III) ions, and cationic derivatives of substituted ferrocene, and the like molecules. Suitable metal cationic oxidizers include $Ag^{+1}$, $Pd^{+2}$, $Pt^{+2}$, $Hg^{+2}$, $Hg_2^{+2}$, $Au^+$ and $Cu^+$. Most preferred cationic oxidizers are ferrocenium and $Ag^{+1}$ cations.

Illustrative, but not limiting, examples of oxidizing agents in the preparation of the improved catalysts of this invention are ferrocenium tetra(pentafluorophenyl)borate, gold (I) tetrakis 3,4,5-trifluorophenyl borate, silver tetra(pentafluorophenyl)borate, 1,1'-dimethylferrocenium tetrakis 3,5-bistrifluoromethylphenyl borate and the like.

Similar lists of suitable compounds containing other metals and metalloids which are useful as oxidizing agents (second components) could be made, but such lists are not deemed necessary to a complete disclosure. In this regard, it should be noted that the foregoing list is not intended to be exhaustive and other boron compounds that would be useful as well as useful compounds containing other metals or metalloids would be readily apparent, from the foregoing general equations, to those skilled in the art.

Without wishing to be bound by any particular theory of operation it is believed that the cationic oxidizer causes the molecular oxidation of the Group 4 or Lanthanide metal derivative, and in the process becomes a neutral species. The oxidized metal derivative loses a hydrogen or hydrocarbyl radical (.R) by a unimolecular elimination reaction. Two or more such radicals form a hydrogen molecule or a neutral organic species of the formula $R_x$ where x is an integer greater than or equal to 2. These byproducts are of course neutral or noninterfering with any subsequent polymerization reaction and may also be removed from the reaction mixture. This result is much preferred to previously known processes for catalyst activation which resulted in the formation of an amine or similar reaction byproduct.

It should be noted that the two compounds combined for preparation of the active catalyst must be selected so as to avoid transfer of a fragment of the anion, particularly an aryl group, to the metal cation, thereby forming a catalytically inactive species. This could be done by steric hindrance, resulting from substitutions on the groups attached to the Group4 or Lanthanide metal as well as substitutions on the aromatic carbon atoms of the anion. It follows, then, that Group 4 and Lanthanide metal compounds (first components) comprising, e.g., perhydrocarbyl-substituted cyclopentadienyl radicals could be effectively used with a broader range of second compounds than could first components comprising less bulky radicals. As the amount and size of the metal substituents are reduced, however, more effective catalysts are obtained with second compounds containing anions which are more resistant to degradation, such as those with substituents on the meta and/or para positions of the phenyl rings. Another means of rendering the anion more resistant to degradation is afforded by fluorine substitution, especially perfluoro-substitution, in the anion. Second components containing fluoro-substituted stabilizing anions may, then, be used with a broader range of first components.

In general, the catalyst can be prepared by combining the two components in a suitable solvent at a temperature within the range from about −100° C. to about 300° C. The catalyst may be used to polymerize α-olefins and/or acetylenically unsaturated monomers having from 2 to about 18 carbon atoms and/or diolefins having from 4 to about 18 carbon atoms either alone or in combination. The catalyst may also be used to polymerize α-olefins, diolefins and/or acetylenically unsaturated monomers in combination with other unsaturated monomers. In general, the polymerization may be accomplished at conditions well known in the prior art for Ziegler-Natta or Kaminsky-Sinn type polymerization reactions i.e. temperatures from 0°–250° C. and pressures from atmospheric to 1000 atmospheres. Suspension, solution, slurry or other process condition may be employed if desired. A support may be employed but preferably the catalysts are used in a homogeneous manner. It will, of course, be appreciated that the catalyst system will form in situ if the components thereof are added directly to the polymerization process and a suitable solvent or diluent, including condensed monomer, is used in said polymerization process. It is, however, preferred to form the catalyst in a separate step in a suitable solvent prior to adding the same to the polymerization mixture.

As indicated supra, the improved catalyst of the present invention will, preferably, be prepared in a suitable solvent or diluent. Suitable solvents or diluents include any of the solvents known in the prior art to be useful as solvents in the polymerization of olefins, diolefins and acetylenically unsaturated monomers. Suitable solvents include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, perfluorinated hydrocarbons such as perfluorinated $C_{4-10}$ alkanes, and the like and aromatic and alkyl-substituted aromatic compounds such as benzene, toluene, xylene and the like. Suitable solvents also include liquid olefins which may act as monomers or comonomers including ethylene, propylene, butadiene, cyclopentene, 1-hexane, 3-methyl-1-pentene, 4-methyl-1-pentene, 1,4-hexadiene, 1-octene, 1-decene, styrene, divinylbenzene, allylbenzene, vinyltoluene (including all isomers alone or in admixture), and the like.

It is believed that the active catalyst species of the present invention contains a metal center which center remains cationic, unsaturated and has a metal-carbon bond which is reactive with olefins, diolefins and acetylenically unsaturated compounds. Also associated with this metal center is a charge balancing anionic remnant of the formula $A^{-c}$.

The catalyst formed by the method of this invention may be retained in solution or separated from the solvent, isolated, and stored for subsequent use. As previously indicated supra, the catalyst may also be prepared in situ during a polymerization reaction by passing the separate components into the polymerization vessel where the components will contact and react to produce the improved catalyst of this invention.

The equivalent ratio of derivative of a Group 4, or Lanthanide metal compound to oxidizing agent compound employed is preferably in a range from 0.1:1 to 10:1, more preferably from 0.75:1 to 2:1, most preferably 1.0:1.0. In most polymerization reactions the equivalent ratio of catalyst:polymerizable compound employed is from $10^{-12}:1$ to $10^{-1}:1$, more preferably from $10^{-6}:1$ to $10^{-3}:1$.

A beneficial feature of some of the catalysts of this invention, particularly those based on monocyclopentadienyl substituted titanium compounds in combination with an oxidizing agent comprising boron, is that when the catalysts of this invention are used to copolymerize α-olefins, either alone or in combination with diolefins, the amount of higher molecular weight olefin or diolefin incorporated into the copolymer is significantly increased when compared to copolymers prepared with the more conventional Ziegler-Natta type catalysts. The relative rates of reaction of ethylene and higher α-olefins with the aforementioned titanium-based catalysts of this invention are so similar that the monomer distribution in copolymers prepared with the catalysts of this invention may be controlled by the ratio of monomeric reactants.

"Addition polymerizable monomers" usefully polymerized according to the present invention include for example ethylenically unsaturated monomers, acetylenic compounds, conjugated or nonconjugated dienes, polyenes, carbon monoxide, etc. Preferred monomers include the $C_{2-10}$ α-olefins especially ethylene, propylene, isobutylene, 1-butene, 1-hexene, 4-methyl-1-pentene, and 1-octene. Other preferred monomers include styrene, halo- or alkyl substituted styrene, tetrafluoroethylene, vinylbenzocyclobutane, and 1,4-hexadiene.

In general, catalysts can be selected so as to produce polymer products which will be free of certain trace impurities generally found in polymers produced with Ziegler-Natta type catalysts such as aluminum, magnesium, chloride and the like. The polymer products produced with the catalysts of this invention should, then, have a broader range of applications than polymers produced with more conventional Ziegler-Natta type catalysts comprising a metal alkyl such as an aluminum alkyl.

Having described the invention the following examples are provided as further illustration thereof and are not to be construed as limiting. Unless stated to the contrary all parts and percentages are expressed on a weight basis.

EXAMPLE 1

A catalyst mixture was prepared by combining 50 micromoles of bis(cyclopentadienyl)dibenzylzirconium and 50 micromoles of ferrocenium perfluorotetraphenyl borate in 50 ml purified and deaerated toluene. The mixture was agitated for approximately 30 seconds until the blue ferrocenium coloration was discharged.

EXAMPLE 2

To 25 ml of deaerated purified toluene 25 micromoles of (tert-butylamido)dimethyl(tetramethyl-$\eta^5$ cyclopentadienyl)silanedibenzylzirconium and 25 micromoles of ferroceniumperfluorotetraphenyl borate were added. The mixture was agitated for approximately 1 minute until the blue color of the solid ferrocenium salt was discharged.

Polymerization 1

The catalyst of Example 1 was combined with a mixture comprising 2 L of mixed alkane solvent (Isopar E ™ available from Exxon Chemicals Inc.), 75 ml at 50 psi of hydrogen, and ethylene (31 atmospheres) in a 4 L reactor. The reactants were previously deaerated and purified and the reactor contents were heated to 170° C. Ten milliliters of the catalyst solution of Example 1 were added. An immediate rapid uptake of ethylene and considerable rise in reactor temperature occurred. (The ethylene uptake was greater than 100 g per minute and the temperature rise was greater than 17° C.). At the end of a 10 minute reaction period the reactor contents were removed and devolatilized leaving 46 g of high density polyethylene.

Polymerization 2

Copolymers of ethylene and 1-octene were prepared utilizing the catalysts of Example 2. A 4 L reactor was charged with 2 L of mixed alkane solvent (Isopar E ™) and 300 ml of 1-octene, heated to 150° C. and pressurized with ethylene to 31 atmospheres. All components had been previously deaerated and purified. 20 ml of the catalyst solution of Example 2 were added resulting in an immediate rapid uptake of ethylene and a large rise in reactor temperature (approximately 50 g per minute ethylene uptake and temperature rise of 26° C.). At the end of a 10 minute period the reactor contents were removed and devolatilized leaving 78 g of ethylene/1-octene copolymer. The 1-octene content of the polymer was 7.5 mole % as determined by mass balance.

What is claimed is:

1. A composition useful as a catalyst in addition polymerizations and substantially lacking in byproducts that interfere with the polymerization process, said composition corresponding to the formula:

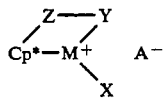

wherein:
M is a metal of Group 4 or the Lanthanide series of the Periodic Table of Elements;
Cp* is cyclopentadienyl group wherein each carbon atom in the cyclopentadienyl radical may be unsubstituted or substituted with the same or a different radical selected from the group consisting of $C_{1-20}$ hydrocarbyl radicals, $C_{1-20}$ substituted hydrocarbyl radicals wherein one or more hydrogen atoms of the hydrocarbyl group is replaced by a halogen atom, $C_{1-20}$ hydrocarbyl substituted metalloid radicals wherein the metalloid is selected from Group 14 of the Periodic Table of Elements, and halogen radicals; or two or more such substituents may together form a fused ring system;
Z is a divalent moiety comprising oxygen, boron, or a member of Group 14 of the Periodic Table of the Elements;
Y is a linking group comprising nitrogen phosphorus, oxygen, or sulfur or optionally Z and Y together form a fused ring system;
X is hydride or a $C_{1-10}$ hydrocarbyl group; and
$A^-$ is a monovalent compatible, noncoordinating anion corresponding to the formula:

$[BX_1X_2X_3X_4]^-$ wherein $X_1$ to $X_4$ are the same of different nonreactive, organyl or silyl radicals containing from 6 to 20 carbon or silicon atoms and lacking in reactive hydrogen moieties, and two or more of $X_1$ to $X_4$ may be linked to each other through a stable bridging group.

2. A composition according to claim 1 wherein M is titanium or zirconium.

3. A composition according to claim 1 wherein $A^-$ is:

$[BX_1X_2X_3X_4]^-$ wherein:
B is boron in a valence state of 3.
$X_1$ to $X_4$ are the same or different nonreactive, organyl or silyl radicals containing from 6 to 20 carbon or silicon atoms and optionally two or more of $X_1$ to $X_4$ may be linked to each other through a stable bridging group.

4. A composition according to claim 3 wherein $X_1$, $X_2$, $X_3$, and $X_4$ are perfluorinated hydro radicals containing from 1 to 20 carbons.

5. A process for preparing a composition useful as a catalyst in addition polymerizations and substantially lacking in byproducts that interfere with the polymerization process, said composition corresponding to the formula:

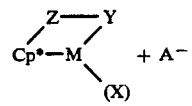

wherein:
M is a metal of Group 4 or the Lanthanide series of the Periodic Table of Elements;
Cp* is cyclopentadienyl group wherein each carbon atom in the cyclopentadienyl radical may be unsubstituted or substituted with the same or a different radical selected from the group consisting of $C_{1-20}$ hydrocarbyl radicals, $C_{1-20}$ substituted hydrocarbyl radicals wherein one or more hydrogen atoms of the hydrocarbyl group is replaced by a halogen atom, $C_{1-20}$ hydrocarbyl substituted metalloid radicals wherein the metalloid is selected from Group 14 of the Periodic Table of Elements, and halogen radicals; or two or more such substituents may together form a fused ring system;
Z is a divalent moiety comprising oxygen, boron, or a member of Group 14 of the Periodic Table of the Elements;
Y is a linking group comprising nitrogen phosphorus, oxygen, or sulfur or optionally Z and Y together form a fused ring system;
X is hydride or a $C_{1-10}$ hydrocarbyl group; and
$A^-$ is a monovalent compatible, noncoordinating anion corresponding to the formula:

$[BX_1X_2X_3X_4]^-$ wherein $X_1$ to $X_4$ are the same of different nonreactive, organyl or silyl radicals containing from 6 to 20 carbon or silicon atoms and lacking in reactive hydrogen moieties, and two or more of $X_1$ to $X_4$ may be linked to each other through a stable bridging group, said process comprising contacting a derivative of a Group 4 or Lanthanide metal corresponding to the formula:

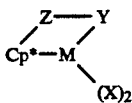

wherein Cp*, Z, Y, M and X are as previously defined;

with an oxidizing agent which in reduced form is noninterfering with the resulting catalyst, said oxidizing agent comprising a cationic oxidizer and a compatible noncoordinating anion and corresponding to the formula:

$$(Ox^{+a})_b(A^-)_d$$

wherein $Ox^{+a}$ is a cationic oxidizer having a charge of $+a$ comprising an organic or inorganic ion having an oxidation potential sufficient to cause molecular oxidation of the metal derivative so as to form a catalytic species;

b and d are integers selected to provide charge balance;

and $A^-$ is as previously defined.

6. A process according to claim 5 wherein the derivative of a Group 4 or Lanthanide metal corresponds to the formula:

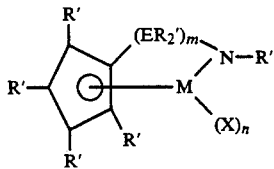

wherein:

M is a metal of Group 4 or the Lanthanide series of the Periodic Table of the Elements;

r' each occurrence is independently selected from the group consisting of hydrogen, silyl, alkyl, aryl and combinations thereof having up to 10 carbon or silicon atoms;

X independently each occurrence is hydride, alkyl or aryl of up to 10 carbons;

m is 1 or 2; and n is 1 or 2 depending on the valence of M.

7. A process according to claim 5 wherein M is titanium or zirconium.

8. A process according to claim 5 wherein $A^-$ is:

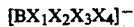

$$[BX_1X_2X_3X_4]^-$$

wherein:

B is boron in a valence state of 3, $X_1$ to $X_4$ are the same or different nonreactive, organyl or silyl radicals containing from 6 to 20 carbon or silicon atoms and optionally two or more of $X_1$ to $X_4$ may be linked to each other through a stable bridging group.

9. A process according to claim 8 wherein $X_1$, $X_2$, $X_3$, and $x_4$ are perfluorinated hydro radicals containing from 1 to 20 carbons.

10. A process according to claim 5 wherein $Ox^{+a}$ is ferrocenium or $Ag^{+1}$.

11. A process according to claim 5 wherein M is titanium or zirconium.

12. In a catalytic addition polymerization process wherein one or more addition polymerizable monomers selected from the group consisting of ethylene, propylene, isobutylene, 1-butene, 1-hexene, 4-methyl-1-pentene and 1-octene are contacted with a catalyst and the resulting polymer recovered therefrom, the improvement wherein the catalyst is a composition according to claim 1 or 2.

13. A process according to claim 12 wherein addition polymerizable monomers selected from the group consisting of ethylenically unsaturated monomers, acetylenic compounds, carbon monoxide, and mixtures thereof are polymerized.

14. A process according to claim 3 wherein the ethylenically unsaturated monomers are selected from the group consisting of $\alpha$-olefins having from 2 to 18 carbons, diolefins having from 4 to 18 carbons, styrene and tetrafluoroethylene.

15. A process according to claim 13 wherein the monomers are ethylene or a mixture of ethylene and 1-octene.

16. A process according to claim 12 wherein the catalyst is supported.

17. A process according to claim 12 wherein the catalyst is prepared in situ.

18. In a catalytic addition polymerization process wherein one or more addition polymerizable monomers selected from the group consisting of ethylene, propylene, isobutylene, 1-butene, 1-hexene, 4-methyl-1-pentene and 1-octene are contacted with a catalyst and the resulting polymer recovered therefrom, the improvement wherein the catalyst is a composition prepared according to the process of claim 5, 6 or 7.

19. A process according to claim 18 wherein addition polymerizable monomers selected from the group consisting of ethylenically unsaturated monomers, acetylenic compounds, carbon monoxide, and mixtures thereof are polymerized.

20. A process according to claim 19 wherein the ethylenically unsaturated monomers are selected from the group consisting of $\alpha$-olefins having from 2 to 18 carbons, diolefins having from 4 to 18 carbons, styrene and tetrafluoroethylene.

21. A process according to claim 19 wherein the monomers are ethylene or a mixture of ethylene and 1-octene.

22. A process according to claim 18 wherein the catalyst is supported.

23. A process according to claim 18 wherein the catalyst is prepared in situ.

* * * * *

UNITED STATES PATENT AND TRADEMARK OFFICE
CERTIFICATE OF CORRECTION

PATENT NO. : 5,321,106
DATED : June 14, 1994
INVENTOR(S) : Robert E. LaPointe

It is certified that error appears in the above-identified patent and that said Letters Patent is hereby corrected as shown below:

Column 12, line 27, "hydro" should read -- hydrocarbyl --.

Col. 13, lines 33-42, delete the following formula:

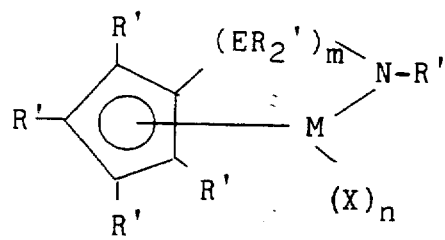

and insert therefor the following formula:

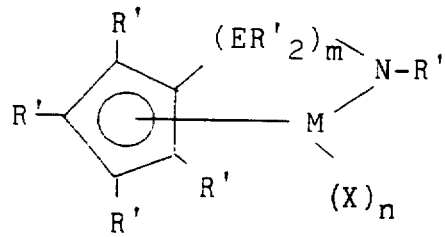

UNITED STATES PATENT AND TRADEMARK OFFICE
CERTIFICATE OF CORRECTION

PATENT NO. : 5,321,106

DATED : June 14, 1994

INVENTOR(S) : Robert E. LaPointe

It is certified that error appears in the above-identified patent and that said Letters Patent is hereby corrected as shown below:

Col. 14, line 5, "$x_4$ should read -- $X_4$ --.

Col. 14, line 5, "hydro" should read -- hydrocarbyl --.

Col. 14, line 24, "3" should read -- 13 --.

Signed and Sealed this

Twenty-fifth Day of October, 1994

Attest:

Attesting Officer

BRUCE LEHMAN

Commissioner of Patents and Trademarks